United States Patent
An et al.

(10) Patent No.: US 10,893,824 B2
(45) Date of Patent: Jan. 19, 2021

(54) HEART FAILURE DETECTION WITH A SEQUENTIAL CLASSIFIER

(75) Inventors: Qi An, Blaine, MN (US); Yi Zhang, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 446 days.

(21) Appl. No.: 13/306,343

(22) Filed: Nov. 29, 2011

(65) Prior Publication Data

US 2012/0157856 A1 Jun. 21, 2012

Related U.S. Application Data

(60) Provisional application No. 61/425,044, filed on Dec. 20, 2010.

(51) Int. Cl.
*A61B 5/08* (2006.01)
*A61B 5/053* (2006.01)
(Continued)

(52) U.S. Cl.
CPC ............ *A61B 5/0816* (2013.01); *A61B 5/024* (2013.01); *A61B 5/0538* (2013.01); *G06F 19/00* (2013.01);
(Continued)

(58) Field of Classification Search
CPC ..... A61B 5/0816; A61B 5/0538; A61B 5/024; A61B 5/0205; A61B 7/006; G06F 19/3418; G06F 19/345; G06F 19/3481
See application file for complete search history.

(56) References Cited

U.S. PATENT DOCUMENTS

| 4,686,987 A | 8/1987 | Salo et al. |
|---|---|---|
| 5,284,136 A | 2/1994 | Hauck |

(Continued)

FOREIGN PATENT DOCUMENTS

| JP | 2004136105 | 5/2004 |
|---|---|---|
| JP | 2006170751 | 6/2006 |

(Continued)

OTHER PUBLICATIONS

"PCT International Search Report and Written Opinion", from International Application No. PCT/US2011063438, dated May 7, 2012, 10 pages.

(Continued)

*Primary Examiner* — Jacqueline Cheng
*Assistant Examiner* — Tho Q Tran
(74) *Attorney, Agent, or Firm* — Schwegman Lundberg & Woessner, P.A.

(57) ABSTRACT

A system and method for automatically analyzing heart failure in a patient, including collecting physiological data from a patient using at least a first sensor and a second sensor to collect two or more sensor measurements, and calculating a first composite value based on at least a first sensor measurement wherein the first composite value is an indication of a likelihood that the patient's heart failure status has changed. If the first composite value is outside of a first specified range, then a second composite value is calculated based on at least a second sensor measurement, wherein the second composite value is an indication of a likelihood that the patient's heart failure status has changed. If the second composite value is outside of a second specified range, then an alert of change in heart failure status is generated.

16 Claims, 6 Drawing Sheets

(51) Int. Cl.
- *G16H 50/20* (2018.01)
- *A61B 7/00* (2006.01)
- *A61B 5/0205* (2006.01)
- *A61B 7/04* (2006.01)
- *A61B 5/024* (2006.01)
- *G06F 19/00* (2018.01)

(52) U.S. Cl.
CPC ......... *G06F 19/3418* (2013.01); *G16H 50/20* (2018.01); *A61B 5/0205* (2013.01); *A61B 7/006* (2013.01); *A61B 7/04* (2013.01); *G06F 19/3481* (2013.01)

(56) References Cited

U.S. PATENT DOCUMENTS

| | | | |
|---|---|---|---|
| 5,342,406 A | 8/1994 | Thompson | |
| 5,935,081 A | 8/1999 | Kadhiresan | |
| 5,957,861 A | 9/1999 | Combs et al. | |
| 6,064,910 A * | 5/2000 | Andersson | A61B 7/003 600/528 |
| 6,076,015 A | 6/2000 | Hartley et al. | |
| 6,336,903 B1 | 1/2002 | Bardy | |
| 6,512,949 B1 | 1/2003 | Combs | |
| 6,599,250 B2 | 7/2003 | Webb et al. | |
| 6,666,826 B2 | 12/2003 | Salo et al. | |
| 6,811,537 B2 | 11/2004 | Bardy | |
| 6,908,437 B2 | 6/2005 | Bardy | |
| 6,978,182 B2 | 12/2005 | Mazar et al. | |
| 7,127,290 B2 | 10/2006 | Girouard et al. | |
| 7,272,443 B2 | 9/2007 | Min et al. | |
| 7,314,451 B2 | 1/2008 | Halperin et al. | |
| 7,395,216 B2 | 7/2008 | Rosenfeld et al. | |
| 7,433,853 B2 | 10/2008 | Brockway et al. | |
| 7,775,983 B2 * | 8/2010 | Zhang et al. | 600/483 |
| 7,993,280 B2 * | 8/2011 | Zhang et al. | 600/529 |
| 8,033,998 B2 | 10/2011 | Bullens et al. | |
| 8,282,562 B2 * | 10/2012 | Koh | 600/484 |
| 8,372,012 B2 * | 2/2013 | Averina et al. | 600/483 |
| 2002/0068745 A1 * | 6/2002 | Levy | C07D 473/34 514/263.2 |
| 2003/0125774 A1 | 7/2003 | Salo | |
| 2004/0116819 A1 * | 6/2004 | Alt | A61B 5/0031 600/513 |
| 2004/0127792 A1 | 7/2004 | Siejko et al. | |
| 2004/0230127 A1 | 11/2004 | Bardy | |
| 2005/0234352 A1 | 10/2005 | Bardy | |
| 2006/0010090 A1 | 1/2006 | Brockway et al. | |
| 2006/0064030 A1 * | 3/2006 | Cosentino | G16H 40/63 600/547 |
| 2006/0129194 A1 * | 6/2006 | Zhang | A61N 1/3712 607/17 |
| 2006/0247702 A1 * | 11/2006 | Stegemann | A61N 1/36585 607/17 |
| 2007/0073168 A1 | 3/2007 | Zhang et al. | |
| 2007/0213599 A1 * | 9/2007 | Siejko | A61B 5/00 600/300 |
| 2007/0260285 A1 * | 11/2007 | Libbus | A61B 5/0031 607/9 |
| 2008/0161657 A1 * | 7/2008 | Bullens et al. | 600/301 |
| 2009/0076344 A1 | 3/2009 | Libbus et al. | |
| 2010/0094102 A1 | 4/2010 | Zhang et al. | |
| 2010/0113888 A1 | 5/2010 | Cho et al. | |
| 2010/0185262 A1 * | 7/2010 | Kuhn | A61B 5/14542 607/60 |
| 2010/0204550 A1 * | 8/2010 | Heneghan | A61B 5/0205 600/301 |
| 2011/0022127 A1 * | 1/2011 | Averina | A61B 5/0537 607/62 |
| 2014/0147867 A1 * | 5/2014 | Arnold | G01N 33/6893 435/7.94 |

FOREIGN PATENT DOCUMENTS

| | | |
|---|---|---|
| JP | 2011509764 | 7/2009 |
| WO | WO-2004012815 | 2/2004 |
| WO | WO-2004034903 | 4/2004 |
| WO | 2009094335 | 7/2009 |
| WO | WO-2009082284 | 7/2009 |
| WO | WO-2009094335 | 7/2009 |
| WO | 2010033699 | 3/2010 |
| WO | 2010042790 | 4/2010 |
| WO | WO-2010042790 | 4/2010 |
| WO | WO-2012087559 | 6/2012 |

OTHER PUBLICATIONS

"European Application Serial No. 11799557.1, Examination Notification Art. 94(3) dated Sep. 9, 2015", 4 pgs.

"European Application Serial No. 11799557.1, Office Action dated Aug. 6, 2013", 2 pgs.

"European Application Serial No. 11799557.1, Response filed Jan. 28, 2014 to Office Action dated Aug. 6, 2013", 10 pgs.

"European Application Serial No. 11799557.1, Communication Pursuant to Article 94(3) EPC dated Dec. 21, 2017", 4 pgs.

"European Application Serial No. 11799557.1, Response filed Apr. 26, 2018 to Communication Pursuant to Article 94(3) EPC dated Dec. 21, 2017", 8 pgs.

"European Application Serial No. 11799557.1, Communication Pursuant to Article 94(3) EPC dated Feb. 27, 2019", 3 pgs.

"European Application Serial No. 11799557.1, Response Filed Jun. 25, 2019 to Communication Pursuant to Article 94(3) EPC dated Feb. 27, 2019", 8 pgs.

"International Preliminary Report on Patentability," for PCT/US2011/063438, dated Jul. 4, 2013 (5 pages).

"Office Action," for Japanese Patent Application No. 2013546183, dated Jul. 25, 2014 (5 pages) with English translation.

* cited by examiner

HEART FAILURE DETECTION WITH A SEQUENTIAL CLASSIFIER

This application claims the benefit of U.S. Provisional Application No. 61/425,044, filed Dec. 20, 2010, the contents of which are herein incorporated by reference.

TECHNICAL FIELD

This disclosure relates generally to systems and methods for analyzing data from a medical device, and, more particularly, to medical systems and methods that can be used to analyze cardiac signal data.

SUMMARY OF THE INVENTION

Embodiments of the invention are related to medical systems and methods that can be used to analyze and collect information from medical devices, amongst other things.

In one embodiment, a method for detecting heart failure in a patient includes collecting physiological data from a patient using at least a first sensor and a second sensor to collect two or more sensor measurements, and calculating a first composite value based on at least a first sensor measurement wherein the first composite value is an indication of a likelihood that the patient's heart failure status has changed. If the first composite value is outside of a first specified range, then a second composite value is calculated based on at least a second sensor measurement, wherein the second composite value is an indication of a likelihood that the patient's heart failure status has changed. If the second composite value is outside of a second specified range, then an alert of change in heart failure status is generated, wherein the alert includes an indication of a likelihood that the patient's heart failure status has worsened. The first and second specified ranges can be modified.

In another embodiment, a system for detecting heart failure in a patient, includes a first sensor and a second sensor to collect two or more sensor measurements of physiological data from a patient and a processor configured to calculate a first composite value based on at least a first sensor measurement wherein the first composite value is an indication of a likelihood that the patient's heart failure status has changed. The processor is further configured to calculate a second composite value based on at least a second sensor measurement if the first composite value is outside of a first specified range, wherein the second composite value is an indication of a likelihood that the patient's heart failure status has changed. The system further includes a communication module configured to generate an alert of change in heart failure status if the second composite value is outside of a second specified range, wherein the alert includes an indication of a likelihood that the patient's heart failure status has worsened. The system further includes a range modification module configured to modify the first and second specified ranges.

In yet another embodiment, a method of detecting heart failure in a patient includes collecting physiological data from a patient using at least a first sensor and a second sensor to collect two or more sensor measurements, where the first and second sensors reside on a cardiac rhythm management device, and where the first sensor is a respiration rate sensor and the second sensor is a trans-thoracic impedance sensor. Another step of the method is calculating a first composite value based on at least a first sensor measurement wherein the first composite value is an indication of a likelihood that the patient's heart failure status has changed. If the first composite value is outside of a first specified range, then calculating a second composite value based on at least a second sensor measurement, wherein the second composite value is an indication of a likelihood that the patient's heart failure status has changed. If the second composite value is outside of a second specified range, generating an alert of change in heart failure status, wherein the alert includes an indication of a likelihood that the patient's heart failure status has worsened. In this method, the first and second specified ranges can be modified by a caregiver, the first composite value is calculated based on current and past values for respiration rate over a period of time, and the second composite value is calculated based on current and past values for trans-thoracic impedance over a period of time.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

Figure 1:
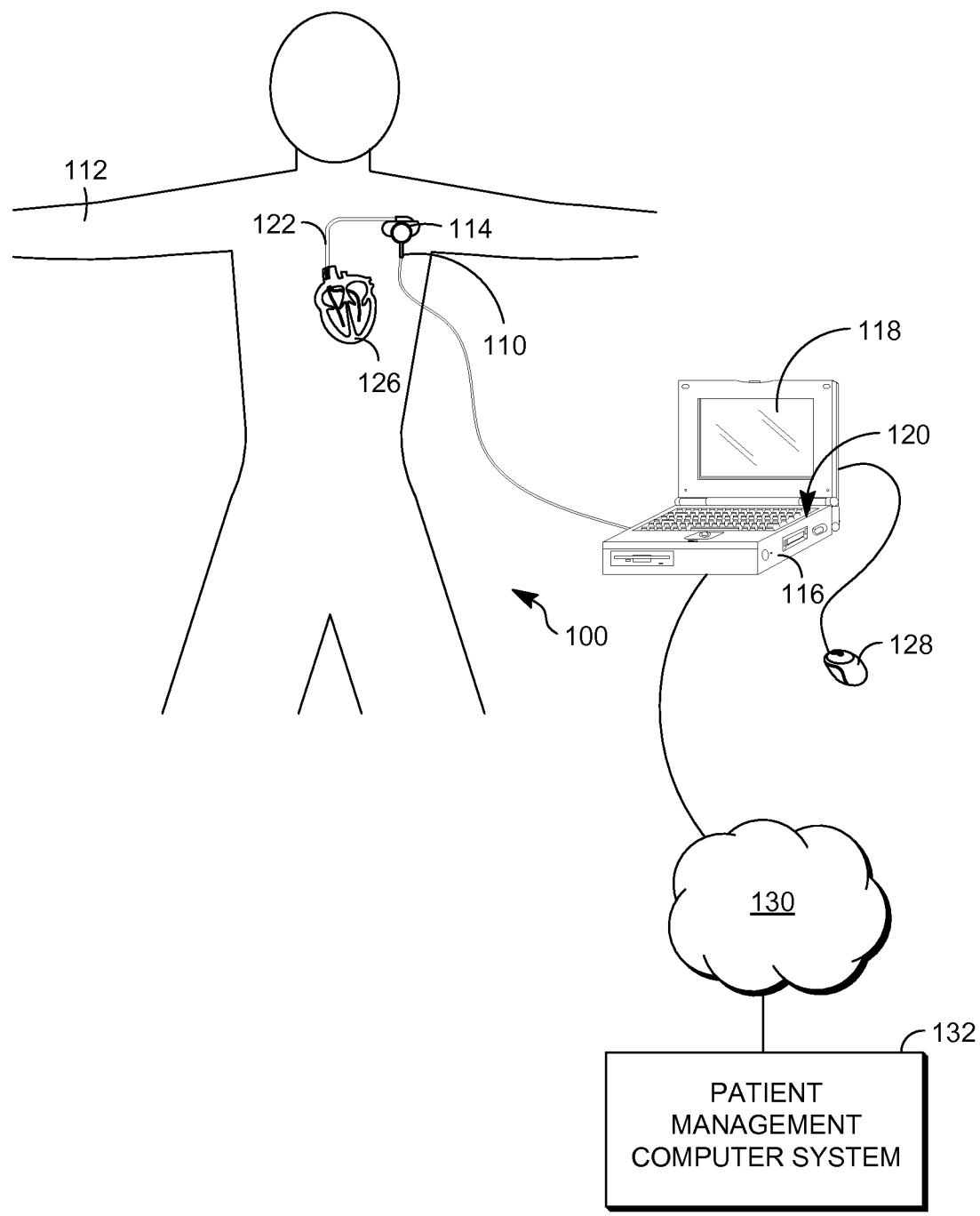
FIG. 1 is a schematic diagram of an exemplary implementation of a cardiac rhythm management (CRM) system, including an implanted CRM device, an external interface device, and a patient management computer system

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

This disclosure relates generally to medical data-generating devices and, more particularly, to systems and methods for analyzing information from such medical devices. In particular, this disclosure relates to systems and methods for detecting heart failure (HF) in a patient using the output of sensors.

Presently, heart failure (HF), also referred to as congestive heart failure, is one of the leading causes of cardiovascular disease-related deaths in the world. Clinically, HF involves circulatory congestion caused by heart disorders that are primarily characterized by abnormalities of left ventricular function and neurohormonal regulation. HF occurs when these abnormalities cause the heart to fail to pump blood at a rate required by the metabolizing tissues. The effects of HF range from impairment during physical exertion to a complete failure of cardiac pumping function at any level of activity. Clinical manifestations of HF include respiratory distress, such as shortness of breath and fatigue, reduced exercise capacity or tolerance, pulmonary and/or peripheral edema, dilated cardiomyapathy, or ventricular dilation. Early attention to signs and symptoms of HF decompensation is needed for the health of the patient and allows early initiation of treatment. However, one of the many challenges in detection of worsening HF is to reduce false alarms while ensuring that actual or true changes in status are detected accurately. The systems and methods described below monitor the patient and generate alerts to the clinician when there is an indication of a worsening in heart failure status. Because the alerts often require a clinician's timely review of patient-related information to determine what triggered the alert and to identify the appropriate response, false alarms cause the unnecessary expenditure of healthcare resources. Additionally, too many false alarms may cause the clinician to pay less attention to all alerts, including detections which are true, thereby defeating the benefit of the system.

Several factors make the early diagnosis and prevention of HF, as well as the monitoring of the progression of HF, relatively difficult. First, the onset of HF is generally subtle and erratic. Often, the symptoms are ignored and the patient compensates by changing his or her daily activities. As a result, many HF conditions or deteriorations in HF remain undiagnosed until more serious problems arise, such as pulmonary edema or cardiac arrest. Moreover, the susceptibility to suffer from HF depends upon the patient's age, sex, physical condition, and other factors, such as diabetes, lung disease, high blood pressure, and kidney function. No one factor is dispositive. Finally, annual or even monthly checkups provide, at best, a "snapshot" of patient wellness and the incremental and subtle clinicophysiological changes which portend the onset or progression of HF often go unnoticed, even with regular health care. Documentation of subtle improvements following therapy, that can guide and refine further evaluation and therapy, can be equally elusive.

Nevertheless, taking advantage of frequently and regularly measured physiological measures, such as recorded manually by a patient, via an external monitoring or therapeutic device, or via implantable device technologies, can provide a degree of detection and prevention.

Patients already suffering from some form of treatable heart disease often are treated using an implantable medical device or a wearable medical device, such as a cardiac rhythm management system (CRM systems) that include an implantable cardiac rhythm management device (CRM device), an external interface device and a patient management computer system. Additionally, some CRMs detect events by monitoring electrical heart activity signals. Some CRMs derive measurements of hemodynamic parameters related to chamber filling and contractions from electrical signals provided by sensors. Examples of CRMs include implantable pulse generators (IPG), cardiovascular or heart failure monitors, therapeutic devices, or similar external wearable device, with which rhythm and structural problems of the heart can be monitored and treated.

One embodiment of a CRM device will now be described with reference to FIG. 1, which is a schematic of an exemplary CRM system 100. The system 100 can include an implantable medical device (IMD) 114 disposed within a patient 112. The implantable medical device 114 can include pacing functionality. The implantable medical device 114 can be of various types such as, for example, a pacemaker, a cardioverter-defibrillator, a cardiac resynchronization device, a heart monitoring device, or the like. In some embodiments, the implantable medical device 114 can include one or more leads 122 disposed in or near the patient's heart 126.

The implantable medical device 114 can be in communication with an external interface system 116. In some embodiments, communication between the implantable medical device 114 and the external interface system 116 can be via inductive communication through a wand 110 held on the outside of the patient 112 near the implantable medical device 114. However, in other embodiments, communication can be carried out via radiofrequency transmission, acoustically, ultrasonically, or the like.

The implantable medical device 114 can include one or more implantable sensors in order to gather data regarding the patient 112. For example, the implantable medical device 114 can include an activity level sensor, a respiration sensor, a heart sounds sensor, a blood pressure sensor, an impedance sensor, or other sensors.

These types of devices are useful for detecting physiological changes in patient conditions through the retrieval and analysis of telemetered signals stored in an on-board, volatile memory. Typically, these devices can store more than thirty minutes of per heartbeat data recorded on a per heartbeat, binned average basis, or on a derived basis from, for example, atrial or ventricular electrical activity, minute ventilation, patient activity score, cardiac output score, heart sound amplitude, intra-thoracic impedance, mixed venous oxygen score, cardiovascular pressure measures, and the like. These telemetered signals can be remotely collected and analyzed using an automated patient care system.

There is a need for a systematic approach to detecting trends in regularly collected physiological data indicative of a change in the HF status of a patient. Examples of a change in the HF status of a patient include the onset, progression, regression, or status quo of HF diagnosed and monitored using an automated, remote patient care system. A status of onset can occur where heart failure has not been previously diagnosed. A status of progression, regression or status quo can occur where heart failure has been previously diagnosed, and the status has worsened, improved or stayed the same, respectively. The physiological data could be data recorded either by an external or an implantable medical device.

An improved method for analyzing heart failure status has been developed where a sequential, two-stage analysis process is utilized. A higher level of confidence was observed in the improved method compared to concatenated classifier methods. One example of a concatenated classifier method is where two different criteria are combined to a single composite value and then compared to a single specified range.

In a first stage of the sequential analysis described herein, a first composite value is generated and is compared to a first specified range. In one example, this first composite value is designed to use data that is particularly sensitive to HF or includes an early marker of HF, or both. In one example, the first composite value is designed to use data that is particularly power-cost-effective.

Only if the first composite value is outside of the specified range is the second stage of the analysis conducted. This first stage of the analysis removes the most highly unlikely candidates for HF status change. In the second stage of the analysis, a second composite value is generated and is compared to a second specified range. In one example, the second composite value is related to later markers of HF or provides a more specific prediction of HF or both.

Figure 2:
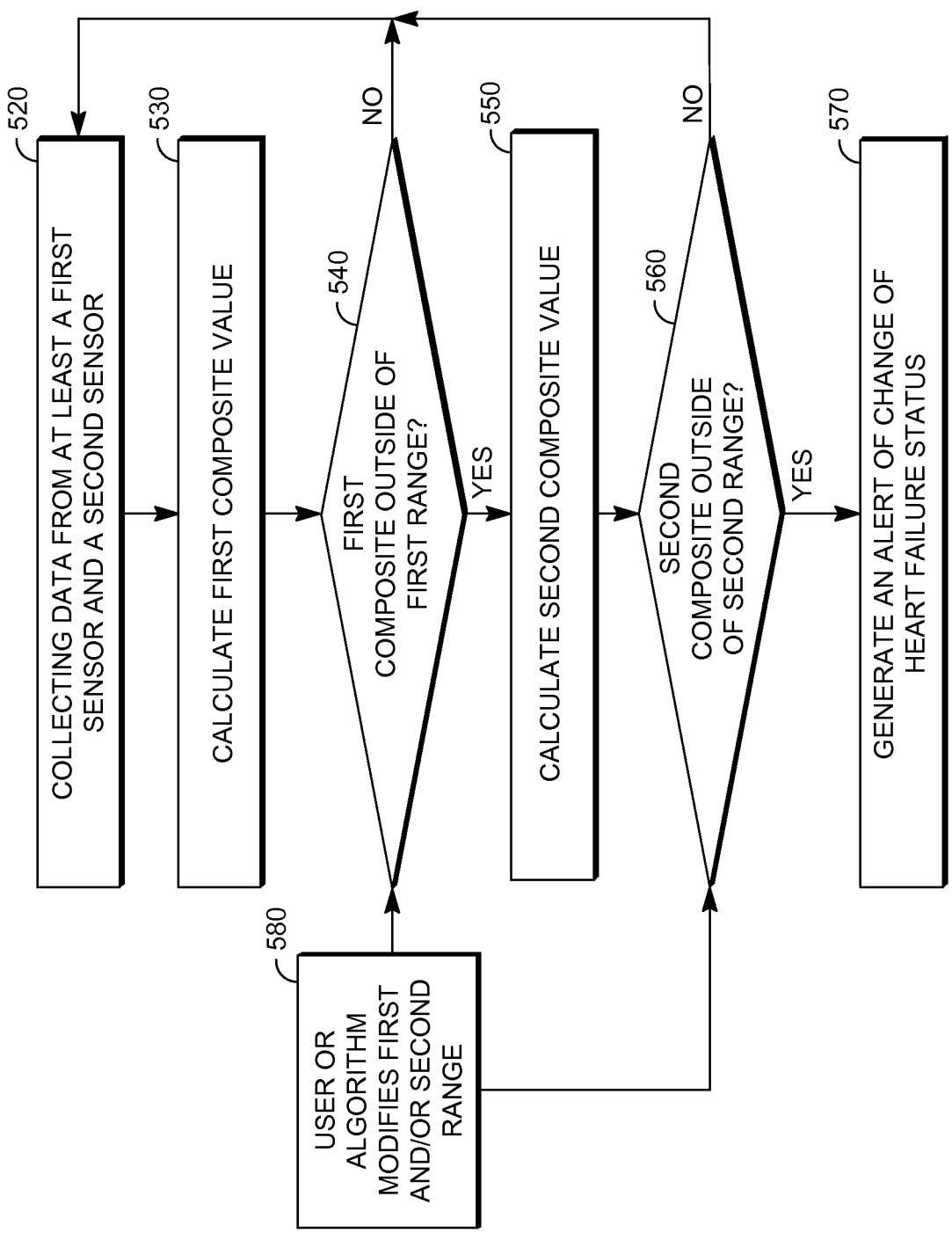
FIG. 2 is a flow chart of the sequential classifier method steps in claim 1.

The steps of the method will now be described with reference to FIG. 2. First, data is collected from at least a first sensor and a second sensor at 520. Then a first composite value is calculated at 530. A composite value is a single value that represents the impact of multiple sensor values, such as values of the same sensor taken at different periods of time, or values from multiple sensors.

Next at step 540, the first composite value is compared to a first specified range. If the first composite value is outside of the range, then the analysis continues with the second stage. If the first composite value is not outside of the range, then the process returns to the beginning to analyze more data or wait for more data.

At step 550, the second composite value is calculated. At step 560, the second composite value is compared to the second specified range. If the second composite is not outside of the range, then the process returns to the beginning to analyze more data or wait for more data. If the second composite value is outside of the range, then the system generates an alert of a change in heart failure status at step 570.

It is possible for the user to modify the first range, the second range or both, at step 580. It is also possible for an algorithm to be used to modify the first range, the second range or both, so that specific patient information is used to generate an appropriate range for the first and second composite values.

In an alternative embodiment of the method steps, the data from the second sensor is not collected until the first criteria is met, in other words, until it is determined that the first composite value is outside of the first range. So the collection of data from a second sensor is removed from step 520, and instead occurs if it is determined that the first composite value is outside of the first range at step 540, and before the second composite value is calculated at step 550.

Many different sensors and sensor readings can provide physiological signals related to the health status of the heart, and can be utilized in the systems and methods described herein.

Figure 3:
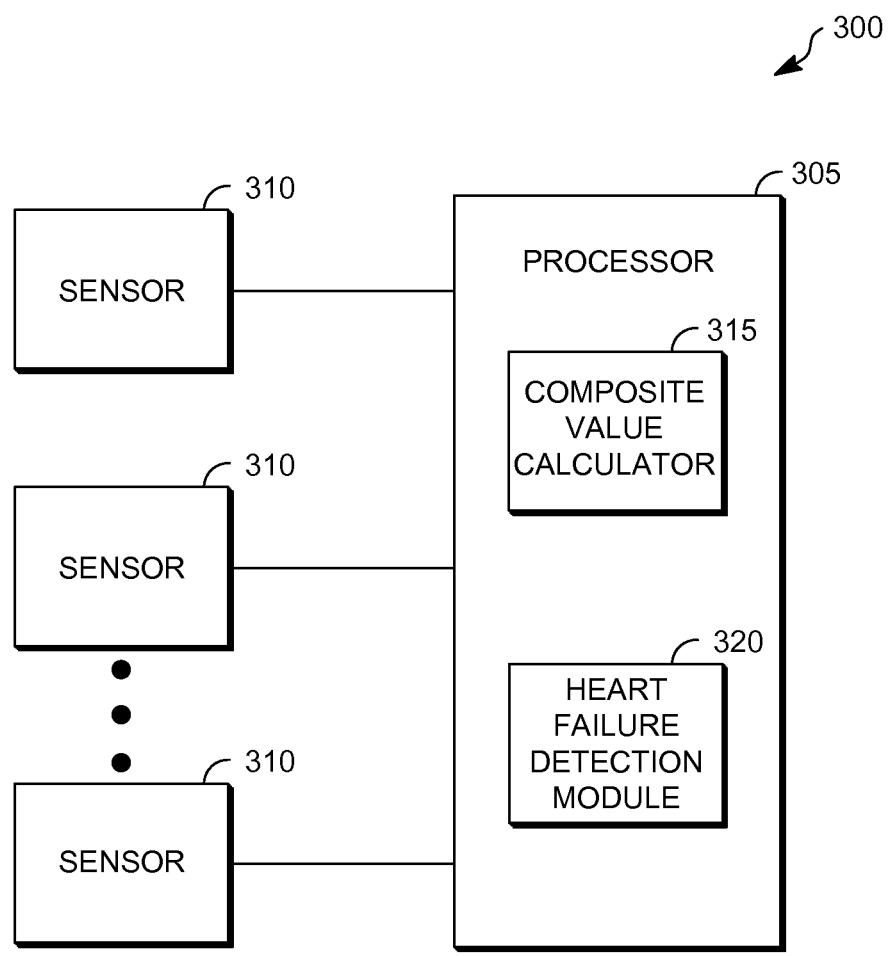
FIG. 3 is a block diagram of an example of a device to monitor heart failure of a patient.

FIG. 3 is a block diagram of an example of a device 300 to monitor HF of a patient or subject. The device 300 includes a processor 305 and a plurality of sensors 310 communicatively coupled to the processor 305. At least one of the sensors 310 is an implantable sensor in one embodiment. In another embodiment, none of the sensors is implanted. The processor 305 may include a microprocessor, a digital signal processor, application specific integrated circuit (ASIC), microprocessor, or other type of processor, interpreting or executing instructions in software or firmware. Each of the sensors 310 provides a sensor signal that includes physiological information. The communicative coupling allows the processor 305 and the sensors 310 to communicate even though there may be intervening circuitry between the processor 305 and the sensors 310.

In some examples, the sensors 310 include an implantable heart sound sensor. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the closing of the aortic valve and the beginning of diastole. The third heart sound (S3) and fourth heart sound (S4) are related to filling pressures of the left ventricle during diastole. A heart sound sensor produces an electrical signal which is representative of mechanical activity of a patient's heart. The heart sound sensor is disposed in a heart, near the heart, or in another location where the acoustic energy can be sensed.

In some examples, the heart sound sensor includes an accelerometer disposed in or near a heart. In another example, the heart sound sensor includes an accelerometer disposed in the IMD. In another example, the heart sound sensor includes a microphone disposed in or near a heart.

Many types of physiological information can be included in a signal provided by a heart sound sensor. For example, the presence of an S3 heart sound may be an indication of elevated filling pressure. Thus, the development of, or a change in, an S3 heart sound may indicate a change in status of HF of the subject. An approach for monitoring heart sounds is found in Siejko et al., U.S. Patent Application Publ. No. 2004/0127792, entitled "Method and Apparatus for Monitoring of Diastolic Hemodynamics," filed Dec. 30, 2002, which is incorporated herein by reference in its entirety.

In some examples, the sensors 310 include a respiration sensor. One example of a respiration sensor is an accelerometer, which can be used to determine respiration rate and other information about respiration. Such an accelerometer can be either implanted or external. One example of a method for determining a respiration signal from an accelerometer signal is described in U.S. Pat. No. 5,935,081, which is incorporated herein by reference in its entirety.

An example of a different implantable respiration sensor is a transthoracic total impedance sensor. The signal provided by the impedance sensor provides physiological information that can be used to measure respiration parameters such as respiratory rate, tidal volume, minute respiration volume, and derived parameters such as the ratio of respiratory rate over tidal volume. An approach to measuring thoracic impedance is described in Hartley et al., U.S. Pat. No. 6,076,015, "Rate Adaptive Cardiac Rhythm Management Device Using Transthoracic Impedance," filed Feb. 27, 1998, which is incorporated herein by reference in its entirety. Measuring respiration parameters can be useful in detecting abnormal breathing.

The sensor signal provided by an impedance sensor can also provide information related to a change in fluid build-up in the thorax region of the subject. A decrease in impedance may indicate an increase in interstitial fluid build-up due to pulmonary edema.

An accelerometer is a more power-efficient sensor than an impedance sensor.

In some examples, the sensors 310 include an implantable patient activity sensor. An example of an implantable patient activity sensor is an accelerometer. The combination of a respiration sensor and an activity sensor, and/or the combination of a heart rate sensor and an activity sensor, is useful for monitoring a patient's physiological response to activity (PRA), such as to detect one or both of abnormal breathing and abnormal reflex sympathetic activation due to activity. The device 300 may include other types of sensors, such as those discussed later in this document.

The processor 305 includes a composite value calculator 315. Modules can be software, hardware, firmware or any combination thereof. Multiple functions can be performed in one or more modules as desired. The composite value calculator 315 determines the value of the composite values based on the data from the sensors 310 for a particular physiological event. A physiological event refers to a time when sensor readings are recorded. A physiological event can also refer to a period of time during which sensor data is recorded.

The processor 305 includes a heart failure (HF) detection module 320. The HF detection module 320 determines whether composite values are indicative of a change in HF status of the patient. To make the determination, the HF detection module 320 includes an algorithm used to evaluate the composite values from the composite value calculator 315. The algorithm includes application of at least one and possibly two rules. The HF detection module 320 determines a likelihood of a change in HF status according to the first and second rules.

The processor 305 can be a part of an implantable medical device or an external medical device.

The method and system described herein uses composite values that are based on sensor measurements. Some previous systems have described identifying heart failure in a patient by looking for an increase in respiration rate, and then looking for a decrease in transthoracic impedance, and then declaring an alert if both are found. However, such a system has lower predictive performance than desired. In contrast, the composite values described herein have been selected and then used in combination to provide higher predictive performance.

First, a pre-screener composite value, also referred to as a first composite value, is calculated. Examples of sensors and sensor readings that are particularly useful during the first stage of screening include sensors that provide earlier indications of heart failure than other sensors. In addition, sensors that are more sensitive to heart failure are useful for calculating the first composite value. By "more sensitive", it is meant that the sensor value is more likely to change in response to the presence of heart failure than other sensor values. For example, sensors that indicate dyspnea, dyspnea upon exertion, tidal volume, respiration rate, plasma renin activity, and rapid shallow breathing index provide earlier and more sensitive indications of heart failure. Examples of earlier indicators of worsening HF, though not necessarily more sensitive indicators, include S3 heart sound, left ventricular diastolic pressure, left atrial pressure, pulmonary artery diastolic pressure, and pulmonary capillary wedge pressure.

In other embodiments, sensor values that are more power-cost-effective are useful for calculating the first stage composite value. Each sensor value requires a certain amount of electrical energy or power to gather one or more raw sensor measurements and calculate the desired sensor reading. Some sensor values require more power than others to gather, calculate and record. For example, a measurement of transthoracic impedance requires more power than the following measurements: respiration rate using an accelerometer, respiration rate using a strain gauge, sensing heart sounds from an accelerometer, measurements from pressure sensors, measurements of activity from an accelerometer, and signals from a cardiac rhythm sensor (EGM). In another example, the measurement of heart sounds using an accelerometer requires more power than measurement of activity using an accelerometer because a more power-intense algorithm is utilized to identify heart sounds.

The sensor values and the specified range for the pre-screener composite value are selected so that the first stage of analysis removes most highly unlikely events. In some embodiments, only a small portion of data will pass the pre-screener stage and be analyzed by the second classifier. If the pre-screener composite value is outside of a specified range, then the second classifier is applied. The second composite value is calculated using more specific markers or later markers of heart failure.

There are many different options for inputs for calculating composite values of sensor readings. A few of these inputs will be described in detail herein, but it is to be understood that these descriptions are not to be limiting on the variety of composite value calculations that are within the system and method described herein.

St_Avg–Lt_Avg@X Days Ago

One specific type of composite value input that was examined for a particular sensor in developing the system and method described herein was long-term and short-term averages difference within a time window, herein after abbreviated "St_avg–Lt_avg@X days ago". To calculate this composite value input, the system first calculates the short term average of the sensor reading. The short-term average is an average over a smaller window of time prior to a reference day than the window of time used for the long term average. In one example, the short-term average is the average value over the previous Y days, such as over the previous 5 days. In another example, the short-term average can be the average value over a window of Y days starting X days before a reference day, such as over a window of 5 days starting 2 days before the reference day. The short-term average can also be the average value over 7 days or 3 days or another value in between.

After calculating the short-term average, the system calculates the long-term average of the sensor reading. The long-term average is an average over a longer window prior to a reference day. In one example, the long-term average is the average value over the previous Z days, such as over the previous 20 days or 15 days. In another example, the long-term average can be the average value over a window of Z days starting X days before the reference day, such as over a window of 20 days starting 2 days before the reference day, or over a window of 15 days, 30 days or a number of days in between.

Then the system subtracts the long-term average from the short-term average to arrive at the input for the composite value.

Lt_Avg–BL@N Days Ago

Another specific type of composite value input for a particular sensor is the long-term average and baseline difference within a time window. To calculate this composite value input, first the long-term average of the sensor reading is calculated as described herein.

Next, the baseline value of the sensor reading is calculated. The baseline value is an average over a fixed window or a window prior to a reference day. In one example, the baseline is the average value over a fixed window, such as over the first 14 days after the patient receives a device. In another example, the baseline can be the average value over a window of L days starting N days before the reference day, such as over a window of 14 days starting 30 days before the reference day, or over a window of 45 days or 60 days, or anywhere in between 14 and 60 days.

Next, the baseline value is subtracted from the long-term average value to arrive at the composite value.

Largest M–Smallest M

Yet another specific type of composite value input is the difference between the largest set of M data points and the smallest set of M data points for a particular sensor reading within a time window. This composite value input allows the system to evaluate how much variation in a particular sensor reading occurs within the time window. In one example, the system identifies the M largest sensor reading values for a time window, such as 20 days, and considers these reading values to be the "largest set". The system identifies the M smallest sensor reading values for the time window and considers these the "smallest set". The system then determines the median of the sensor reading values of each set, and the median of the smallest set is subtracted from the median of the largest set to arrive at a data point. In addition, in this example, the mean of the temporal values of the points in each set can be calculated, and the difference can be determined between the temporal mean of the largest and smallest sets to arrive at another data point, thus producing two data points for the composite value input in this example, where the composite value input is abbreviated "Largest M–Smallest M". If the five largest and five smallest sensor readings are used in the calculation to generate the two data points for the composite value input, then the composite value input is abbreviated "Largest 5–Smallest 5". In one embodiment, a regression model is used to determine the sensor values to use in the first and second composite values based on a database of patient information. A regression model is a statistical model which describes the variation in one or more variables when one or more other variables vary.

In developing the recommendations for first and second composite values described herein, a logistic regression model was used to analyze a database of sensor readings from about two hundred patients, and to determine which sensor readings were most predictive of experiencing a heart failure event. The regression modeling revealed that sensor selection has an impact on the sensitivity and confidence of the predictive algorithm. The regression modeling also revealed that the sequence of the criteria applied in the algorithm also impacts the confidence and sensitivity. Specific and non-limiting examples of composite values will now be described.

In one embodiment, the first sensor is a respiration rate sensor and the first composite value is calculated based on current and past values for respiration rate over a period of time.

One specific composite value that was found to be useful as a pre-screener or first composite value is Lt_avg–BL@19 days for the sensor value reading median respiration rate, which is the median respiration rate over the preceding 24 hour period. Another specific composite value that was found to be useful as a pre-screener or first composite value is Lt_avg–BL@19 days for the sensor value reading maximum respiration rate (MaxRR), where MaxRR rate is the maximum of a median respiration rate of a short window (e.g. 10-30 minutes) over a 24-hour period, 19 days before the reference day. Another specific composite value compares the long-term average and the baseline values for maximum respiration rate at 3 days before the reference day instead of 19 days (Lt_avg–BL@3 days for MaxRR).

Two other specific types of composite values are the difference between the largest set and the smallest set within a time window for Max RR and Med RR, where MedRR is the median of all respiration rates measured over a 24-hour period.

Examples of sensors and sensor readings that are particularly useful during the second stage of screening include indications that are more specific than other indications. In one embodiment, indications used in the second stage composite value occur later in time during the trajectory toward heart failure. In one embodiment, the values used to calculate the second stage composite value are values that require more computational power than other values. Examples include sensors that indicate pulmonary edema—such as trans-thoracic impedance sensors.

Certain implantable medical devices such as defibrillators can take a measurement of transthoracic impedance that is referred to as shock impedance (ShkZ) by measuring the electric potential between the surface of the device and a shock electrode.

Three specific composite values that were found to be useful as second composite values are Lt_avg–BL@19 days, 14 days and 10 days for ShkZ Another useful second composite value is the difference between the largest set and the smallest set within a time window of 24 hours for ShkZ, where each set includes five data points, also expressed as "Largest 5-Smallest 5 for ShkZ" Another useful composite value is St_avg–Lt_avg@17 days ago for ShkZ.

The first and second composite values indicate a likelihood that the patient's heart failure status has changed. The likelihood indication can be a percentage, a decimal, a fraction, or a number on a number scale, among other options.

After the indication of likelihood that a patient's heart failure status has changed is determined for the first composite value, then the first composite value is compared to a first specified range, and if appropriate, the second composite value is compared to a second specified range. In one example, the composite values are each a number between zero and one, and the first specified range is 0 to 0.5. If the first composite value is more than 0.5, then it is outside of the specified range and the method proceeds to calculate the second composite value.

The second specified range in one example is 0 to 0.5, so if the second composite value is more than 0.5 then the system generates an alert of change in heart failure status. The alert includes an indication of a likelihood that the patient's heart failure status has worsened. For example, the alert may indicate that there is a likelihood of 51%, 95% or some other percentage that the patient's heart failure status has worsened.

In another example, the first composite value, second composite value or both are numeric values between 0 and 10, In yet another example, the first composite value, second composite value or both are categorical variables, such as one of very stable, stable, less stable and least stable.

In some embodiments, the system also provides an indication of confidence level in the determination that the patient's heart failure status has worsened, which provides additional information to caregivers which may be useful in treating or further evaluating the patient.

In an example, the confidence level of HF worsening occurring can be determined using one or more regression models. A regression model can relate one or more response variables to one or more predictor variables. A regression model can be expressed as:

$$y = f(x, \beta) + \varepsilon$$

where y represents the one or more response variables, x represents the one or more predictor variables, β represents one or more unknown model parameters, and represents a noise term. Examples of regression models can include, but are not limited to: linear regression models, logistic regression models, artificial neural networks, or decision trees.

In an example, the confidence level of the HF worsening event having occurred can be determined such as by using a linear regression model, which can be expressed as:

$$y = \beta_0 + \beta_1 x_1 + \ldots + \beta_k x_k + \varepsilon,$$

where $\beta_i$, i=0, ... k represents the model parameters that determine the relative contribution of predictor variables $x_i$, i=1, ... k. The model parameters $\beta_i$, i=0, ... k can be determined from a training set by estimation methods, such as a least squares method, a least absolute deviation method, or a maximum likelihood method.

In an example, the confidence level of the HF worsening event having occurred can be determined such as by using a logistic regression model, which can be expressed as:

$$y = \frac{1}{1+e^{-z}},$$

where $z=\beta_0+\beta_1 x_1+\beta_2 x_2+ \ldots +\beta_k x_k$, y is a probability of the HF worsening event having occurred, z is a measure of a total contribution of all of the one or more sensor measurements used, $\beta_0$ is a logistic regression intercept and $\beta_1$, $\beta_2, \ldots, \beta_k$ are the logistic regression coefficients of the one or more sensor measurements $x_1, x_2, \ldots x_k$ respectively.

In one embodiment, the caregiver can adjust the first and second specified ranges according to their observations and experience. In another embodiment, the first and second specified ranges are adjusted by an algorithm based on one or more of the following data: patient population, patient age, patient gender and event information for the patient. In one example, the specified range is adjusted by an algorithm to achieve a desired sensitivity, specificity, positive predictive value, negative predictive value, false positive rate, false negative rate, or any combination of these.

Other sensors, either implantable or external, can be used in the device 300 in FIG. 3 to monitor for HF instead of, or in addition to, those discussed previously. In some examples, the device 300 includes an implantable cardiac pressure sensor to measure chamber pressure of the left ventricle. A decrease in chamber pressure may be indicative of worsening HF.

In an example, a pressure sensor is implanted in a coronary vessel to determine left ventricle pressure by direct measurement of coronary vessel pressure. A description of systems and methods that use such an implantable pressure sensor is found in Salo et al., U.S. Pat. No. 6,666,826, entitled "Method and Apparatus for Measuring Left Ventricular Pressure," filed Jan. 4, 2002, which is incorporated herein by reference in its entirety. Other cardiac pressure sensors examples include a right ventricle (RV) chamber pressure sensor, a pulmonary artery pressure sensor, and a left atrial chamber pressure sensor. A change in heart chamber pressure may also be evident in heart sounds, and therefore a heart sound sensor may be used to deduce a change in pressure.

In some examples, the sensors 310 include an implantable heart rate sensor. In certain example, the heart rate sensor includes the previously mentioned circuits and electrodes to sense an electrogram signal representative of heart depolarizations. A heart sound sensor may be used to sense heart rate as well, such as by measuring intervals between S2 heart sounds for example.

In some examples, the sensors 310 include an implantable oxygen saturation sensor. An oxygen saturation sensor produces an electrical sensor signal proportional to the oxygen saturation of blood, which could be reduced with worsening HF due to inadequate gas exchange in the presence of one or both of pulmonary congestion and decreased oxygen delivery to tissues. An approach for using an implantable sensor to measure blood oxygen saturation levels is found in Thompson, U.S. Pat. No. 5,342,406, entitled "Oxygen Sensor Based Capture Detection for a Pacer," filed Oct. 7, 1992, which is incorporated herein by reference in its entirety.

In some examples, the sensors 310 include an implantable cardiac temperature sensor. In some examples, the implantable cardiac temperature sensor is included in a lead system implanted into the coronary sinus of a patient. The implantable cardiac temperature sensor measures the temperature of the blood returning through the coronary sinus after having passed through myocardial tissue. As a byproduct of normal cardiac function, the heart generates heat. This heat is extracted by the perfusing blood. The blood exits through the coronary veins into the coronary sinus before passing into the right atrium and right ventricle. The blood is then pumped through the lungs where the excess heat is removed and passed out of the body with the exhaled air.

The useful work ($W_u$) performed by the left ventricle relates to the volume of blood moved through the ventricle, whereas the heat output from the left ventricle is related to total work ($W_T$). The difference in temperature between blood entering the left ventricle and blood in a coronary vein is related to left ventricular work. An increase in $W_T$, or cardiac temperature as a surrogate measurement, that is not accompanied by other indications of increased activity or patient exertion may indicate a lowering of efficiency of a patient's hemodynamic system due to worsening HF.

An approach to sensing temperature within a coronary vein is found in Salo, Patent Application Publ. No. 2003/0125774, entitled "Method and Apparatus for Monitoring Left Ventricular Work or Power," filed Dec. 31, 2001, which is incorporated herein by reference in its entirety.

In some examples, the sensors 310 include a blood flow sensor. Examples of a blood flow sensor include a cardiac output sensor circuit or a stroke volume sensor circuit. Examples of stroke volume sensing are discussed in Salo et al., U.S. Pat. No. 4,686,987, "Biomedical Method And Apparatus For Controlling The Administration Of Therapy To A Patient In Response To Changes In Physiologic Demand," filed Mar. 29, 1982, and in Hauck et al., U.S. Pat. No. 5,284,136, "Dual Indifferent Electrode Pacemaker," filed May 13, 1991, which are incorporated herein by reference in their entirety.

Further examples of sensor data are described in Bardy, U.S. Published Application 2005/0234352, "System and method for diagnosing and monitoring congestive heart failure," filed Jun. 10, 2005, which is incorporated herein by reference in its entirety.

Sources of Cardiac Signal Data

One example of a data-generating device is an implantable cardiac rhythm management device. Specific implantable cardiac rhythm management devices include a pacemaker, a cardioverter-defibrillator, a cardiac resynchronization device, a heart rhythm monitoring device, or the like. Other implantable data-generating devices include pressure sensors, heart sound sensors, accelerometers, and impedance sensors. However, it is also possible to generate episode data from external devices, including external pacemakers, external cardioverter-defibrillators, external resynchronization devices, external pressure sensors, external heart sound monitors and external impedance sensors. Additional examples of external devices that monitor cardiac activity include ambulatory electrocardiography devices or Holter monitors, which continuously monitor electrical activity of the heart for 24 hours or more. A data-generating device is one that is capable of providing cardiac signal information for a particular patient.

Many types of CRM devices communicate with devices located outside of the body, which can receive information from the implanted device including sensor information and information about events, such as when the implanted device has provided therapy. In some cases, the external interface device can also transmit operational parameters to an implanted CRM device, that is, program the device.

These external interface devices can be provided to a patient, often in a patient's home, and can collect information from the implanted device, and provide that information to a computer system designed to monitor the patient's status. An exemplary remote patient management system is the LATITUDE® patient management system, available from Boston Scientific Corporation, Natick, Mass. Aspects of exemplary remote patient management and monitoring systems are described in U.S. Pat. No. 6,978,182, the content of which is herein incorporated by reference in its entirety.

The existence of remote patient management systems such as the LATITUDE® patient management system has provided a large amount of data about patients with implanted medical devices. For example, these systems store patient sensor readings including electrocardiogram (EGM), pressure sensor signals, impedance signals and heart sound signals. The sensor readings can include information associated with arrhythmia episodes and other episodes experienced by the patient. These systems also store information about patient characteristics, device settings and delivery of therapy by the device.

"Episode" and "event" are defined to mean activity of a patient's body within a time period of particular interest. The time period can be a time when there is abnormal activity, for example, abnormal cardiac activity. The time period can also be a time lacking in abnormal activity. "Episode data" and "even data" are defined to include sensor readings from a medical data-generating device before, during and after an abnormal episode, and can also include device settings, actions that were taken by the device and other information.

One or more data-generating devices can generate episode data. The episode database may have episode data about a plurality of episodes generated by one device, or generated by multiple devices. In one embodiment, the episode database is external to any of the data-generating devices. However, in another embodiment, the episode database is located within one of the data generating devices.

Description of Hardware Systems

Further detailed embodiments of the hardware of the system will now be described with respect to the attached FIGS.

One embodiment of a data-generating device is a CRM device, as was previously described with reference to FIG. 1. Additional detail related to the CRM system of FIG. 1 will now be provided.

The implantable medical device 114 can be configured to store data over a period of time, and periodically communicate with the external interface system 116 in order to transmit some or all of the stored data.

The external interface system 116 can be for example, a programmer, a programmer/recorder/monitor device, a computer, a patient management system, a personal digital assistant (PDA), or the like. As used herein, the term programmer refers to a device that programs implanted devices, records data from implanted devices, and allows monitoring of the implanted device. Exemplary programmer/recorder/monitor devices include the Model 3120 Programmer, available from Boston Scientific Corporation, Natick, Mass. The external interface system 116 can include a user input device, such as a keyboard 120 and/or a mouse 128. The external interface system 116 can include a video output channel and video output device, such as a video display 118 for displaying video output. The displayed video output can include a user interface screen. In addition, the video display 118 can also be equipped with a touch screen, making it into a user input device as well.

The external interface device 116 can display real-time data and/or stored data graphically, such as in charts or graphs, and textually through the user interface screen. In addition, the external interface device 116 can present textual information to a user along with several response options. The external interface device 116 can also input and store a user's response to a question, and can store a user's text response in some embodiments.

In one embodiment, the external interface device 116, which can also be referred to as a user interface, is in communication with a patient management computer system 132. The communication link between the user interface 116 and the patient management computer system 132 may be via phone lines, the Internet 130, or any other data connection. The user interface 116 can also be used when it is not in communication with a device, but is only in communication with the patient management computer system 132.

In one embodiment, the external interface device 116 is capable of changing the operational parameters of the implantable medical device 114, and is therefore referred to as a programmer. Typically, programmers are used to interface with CRM devices in a clinic or hospital setting. In this context, the user of the external interface device is a physician or trained technician.

Figure 4:
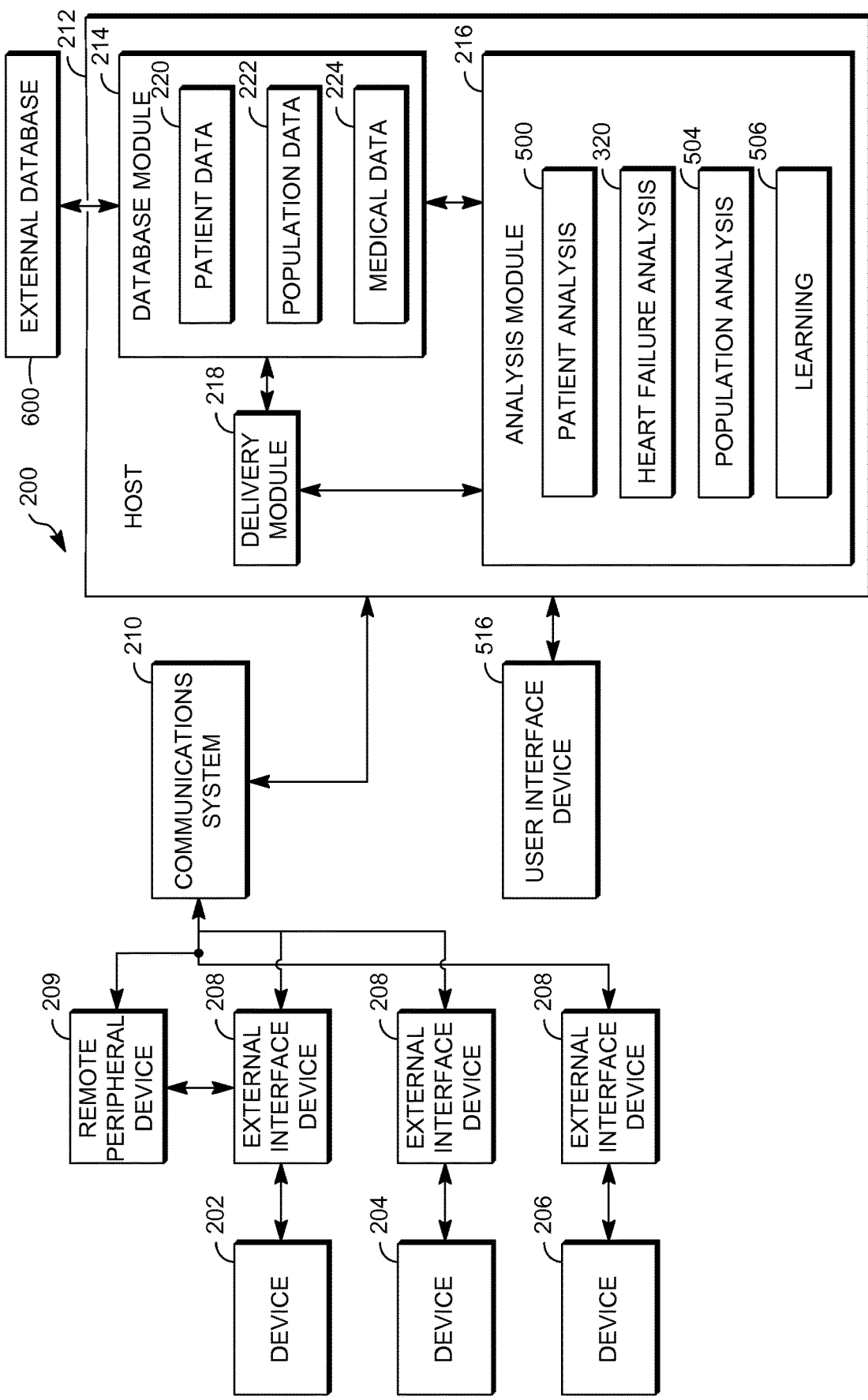
FIG. 4 is a schematic illustration of a patient management system.

FIG. 4 is a schematic illustration of a patient management system consistent with at least one embodiment of the invention. The patient management system is capable of maintaining an episode database using computer storage medium. Examples of computer storage medium include Patient management system 200 generally includes one or more devices 202, 204, and 206, one or more external interface devices 208, a communication system 210, one or more remote peripheral devices 209, and a host 212.

Each component of the patient management system 200 can communicate using the communication system 210. Some components may also communicate directly with one another. The various components of the example patient management system 200 illustrated herein are described below.

Data-generating devices 202, 204, and 206 can be implantable devices or external devices that may provide one or more of the following functions with respect to a patient: (1) sensing, (2) data analysis, and (3) therapy. For example, in one embodiment, devices 202, 204, and 206 are either implanted or external devices used to measure a variety of physiological, subjective, and environmental conditions of a patient using electrical, mechanical, and/or chemical means. The devices 202, 204, and 206 can be configured to automatically gather data or can require manual intervention by the patient or another person. The devices 202, 204, and 206 can be configured to store data related to the physiological and/or subjective measurements and/or transmit the data to the communication system 210 using a variety of methods, described in detail below. Although three devices 202, 204, and 206 are illustrated in the example embodiment shown, many more devices can be coupled to the patient management system. In one embodiment, each of the devices 202, 204 and 206 is serving a different patient. In one embodiment, two or more devices are serving a single patient.

The devices 202, 204, and 206 can be configured to analyze the measured data and act upon the analyzed data. For example, the devices 202, 204, and 206 can be configured to modify therapy or provide an alarm based on the analysis of the data.

In one embodiment, devices 202, 204, and 206 provide therapy. Therapy can be provided automatically or in response to an external communication. Devices 202, 204, and 206 are programmable in that the characteristics of their sensing, therapy (e.g., duration and interval), or communication can be altered by communication between the devices 202, 204, and 206 and other components of the patient management system 200. Devices 202, 204, and 206 can also perform self-checks or be interrogated by the communication system 210 to verify that the devices are functioning properly. Examples of different embodiments of the devices 202, 204, and 206 are provided herein.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance. Derived measurements can also be determined from the implantable device sensors (e.g., a sleep sensor, functional capacity indicator, autonomic tone indicator, sleep quality indicator, cough indicator, anxiety indicator, and cardiovascular wellness indicator for calculating a quality of life indicator quantifying a patient's overall health and well-being).

Devices 202, 204, and 206 can also be external devices, or devices that are not implanted in the human body, that are used to measure physiological data (e.g., a thermometer, sphygmomanometer, or external devices used to measure blood characteristics, body weight, physical strength, mental acuity, diet, heart characteristics, and relative geographic position).

The patient management system 200 may also include one or more remote peripheral devices 209 (e.g., cellular telephones, pagers, PDA devices, facsimiles, remote computers, printers, video and/or audio devices) that use wired or wireless technologies to communicate with the communication system 210 and/or the host 212.

The example database module 214 includes a patient database 400, an episode database 402, an adjudication database 404, a population database 406, and a medical database 408, all of which are described further below. The patient database 400 includes patient specific data, including data acquired by the devices 202, 204, and 206, as well as a patient's medical records and historical information. The population database 406 includes non-patient specific data, such as data relating to other patients and population trends. The example medical database 408 includes clinical data relating to the treatment of diseases, such as historical trend data for multiple patients in the form of a record of progression of their disease(s) along with markers of key events.

The episode database 402 has episode data regarding a plurality of different episodes generated from those of devices 202, 204, and 206 that provide episode data. The adjudication database 404 includes adjudication conclusions associated with the episode data such as arrhythmia episodes. The adjudication database 404 and the episode database 402 can actually be a single database with shared data that is used as either episode data or adjudication data depending on the particular data set being presented to the user.

Information can also be provided from an external source, such as external database 600. For example, the external database 600 could include external medical records maintained by a third party, such as drug prescription records maintained by a pharmacy, providing information regarding the type of drugs that have been prescribed for a patient or, in another example, authorization data from patient groups that have authorized users to view arrhythmia episode data.

The example analysis module 216 includes a patient analysis module 500, a heart failure analysis module 320 as previously discussed herein, population analysis module 504, and a learning module 506. Patient analysis module 500 may utilize information collected by the patient management system 200, as well as information for other relevant sources, to analyze data related to a patient and provide timely and predictive assessments of the patient's well-being. Heart failure analysis module 320 received input from the sensors and calculates a likelihood of worsening heart failure as described herein. Population analysis module 504 uses the data collected in the database module 214 to manage the health of a population. Learning module 506 analyzes the data provided from the various information sources, including the data collected by the patient system 200 and external information sources, and may be implemented via a neural network (or equivalent) system to perform, for example, probabilistic calculations. It is also possible to include a device analysis module which analyzes data from the devices 202, 204, and 206 and external interface devices 208 to predict and determine device issues or failures.

One or more portions of the analysis module 216, such as the heart failure analysis module 320, may be located remotely from other parts of the patient management system 200.

Delivery module 218 coordinates the delivery of reports, patient alerts or programming recommendations based on the analysis performed by the host 212. For example, based on the data collected from the devices and analyzed by the host 212, the delivery module 218 can deliver information to the caregiver, user, or to the patient using, for example, a display provided on the external interface device 208. A user interface device 516 that is independent of a data-generating device may also be used to deliver information. The external interface device 208 and user interface device 516 are also configured, according to multiple embodiments, to display a report, alert, or programming recommendation, receive overwrite information from a user, and receive other data from the user. Displayed data, as described above, can be determined by the heart failure module 320.

External interface devices 208 display information, such as programmer/recorder/monitors, can include components common to many computing devices. User interface devices 516 to display and received information from users can also include components common to many computing devices.

Figure 5:
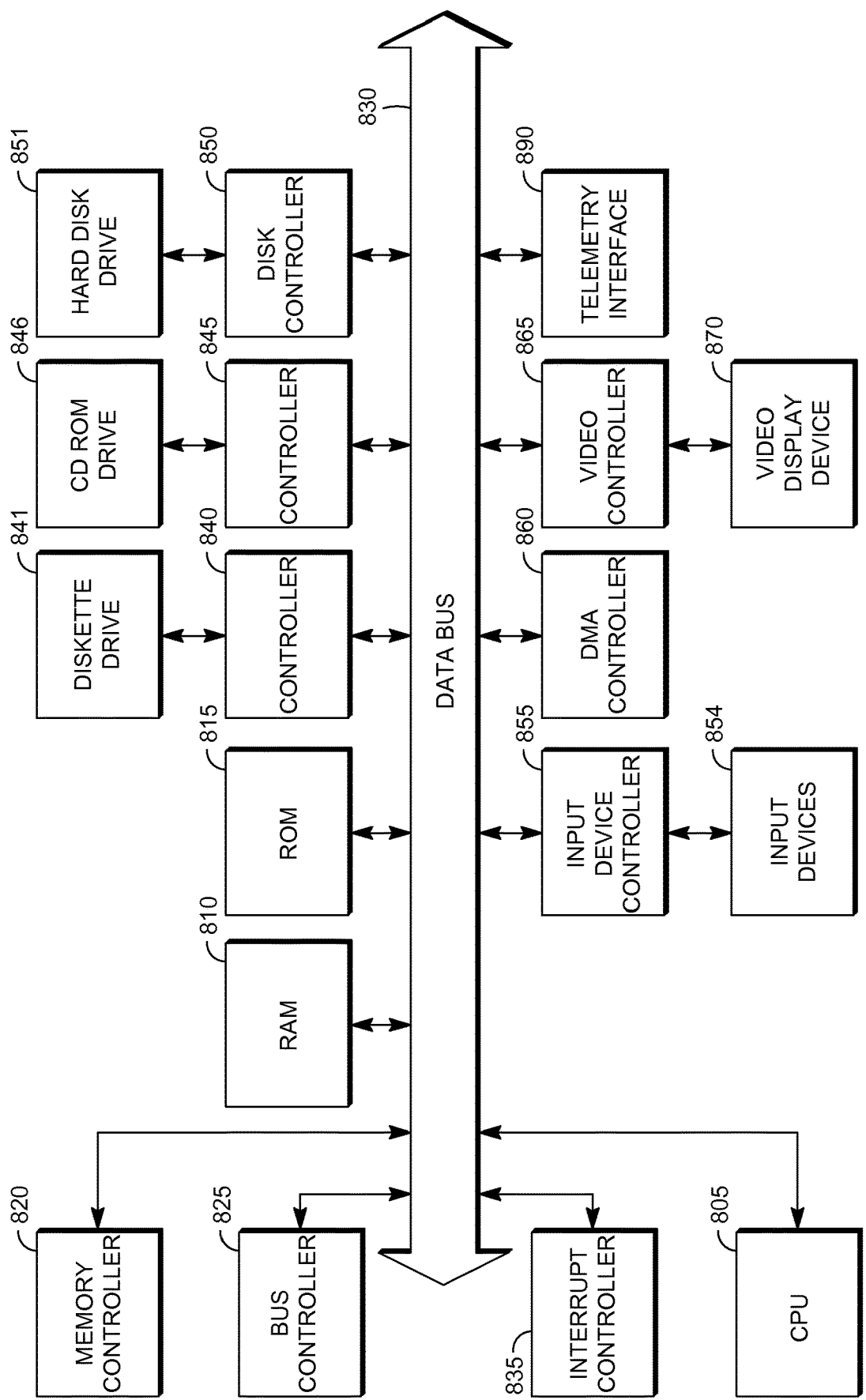
FIG. 5 is a schematic diagram of an implementation of the components of an external interface device such as a programmer.

Referring now to FIG. 5, a diagram of various components is shown in accordance with some embodiments of the invention. However, it is not required that an external interface device have all of the components illustrated in FIG. 5.

In one embodiment, the external interface device includes a central processing unit (CPU) 805 or processor, which may include a conventional microprocessor, random access memory (RAM) 810 for temporary storage of information, and read only memory (ROM) 815 for permanent storage of information. A memory controller 820 is provided for controlling system RAM 810. A bus controller 825 is provided for controlling data bus 830, and an interrupt controller 835 is used for receiving and processing various interrupt signals from the other system components.

Mass storage can be provided by diskette drive 841, which is connected to bus 830 by controller 840, CD-ROM drive 846, which is connected to bus 830 by controller 845, and hard disk drive 851, which is connected to bus 830 by controller 850. User input to the programmer system may be provided by a number of devices. For example, a keyboard and mouse can connected to bus 830 by keyboard and mouse controller 855. DMA controller 860 is provided for performing direct memory access to system RAM 810. A visual display is generated by a video controller 865 or video output, which controls video display 870. The external system can also include a telemetry interface 890 or telemetry circuit which allows the external system to interface and exchange data with an implantable medical device. It will be appreciated that some embodiments may lack various elements illustrated in FIG. 5.

Figure 6:
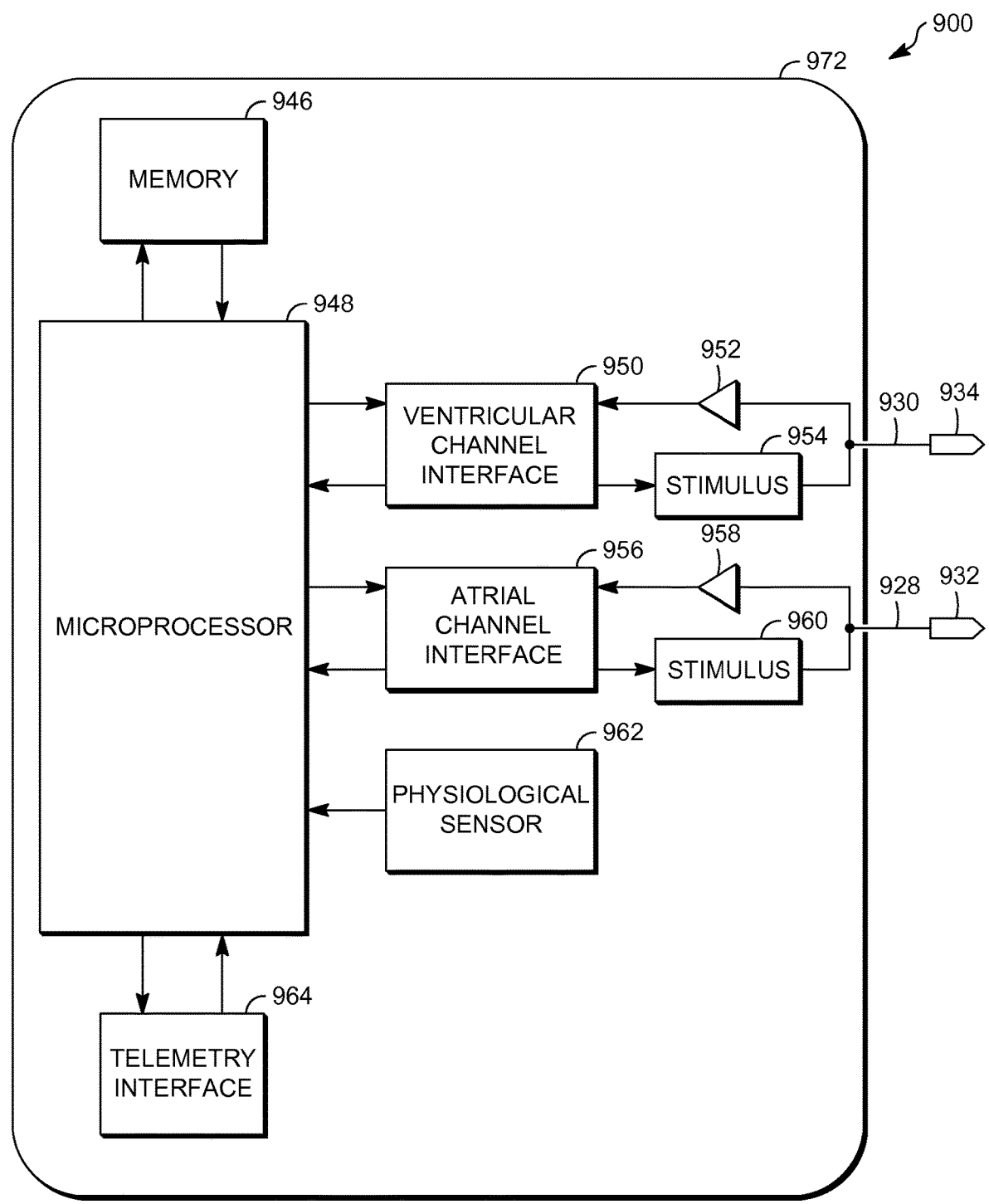
FIG. 6 is a schematic view of components of one example of an implantable device.

Referring now to FIG. 6, some components of an exemplary implantable system 900 are schematically illustrated. The implantable medical system 900 can include an implantable medical device 972 coupled to one or more stimulation leads 930 and 928. The implantable device 972 can also include one or more physiological sensors 962, or other sensors, such as a pressure sensor, impedance sensor and others.

The implantable device can include a microprocessor 948 (or processor) that communicates with a memory 946 via a bidirectional data bus. The processor 948 of the implantable device can include the composite value calculator 315 and the heart failure detection module 320 as described above in relation to FIG. 3, so that the heart failure analysis is performed within the implantable device.

The memory 946 typically comprises ROM or RAM for program storage and RAM for data storage. The implantable device can be configured to execute various operations such as processing of signals and execution of methods as described herein. A telemetry interface 964 is also provided for communicating with an external unit, such as a programmer device or a patient management system.

The implantable device can include ventricular sensing and pacing channels comprising sensing amplifier 952, output circuit 954, and a ventricular channel interface 950 which communicates bidirectionally with a port of microprocessor 948. The ventricular sensing and pacing channel can be in communication with stimulation lead 930 and electrode 934. The implantable device can include atrial sensing and pacing channels comprising sensing amplifier 958, output circuit 960, and an atrial channel interface 956 which communicates bidirectionally with a port of microprocessor 948. The atrial sensing and pacing channel can be in communication with stimulation lead 928 and electrode 932. For each channel, the same lead and electrode can be used for both sensing and pacing. The channel interfaces 950 and 956 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A method of detecting heart failure in a patient via a medical system, comprising:
    collecting sensor measurements of physiological data from a patient using a plurality of sensors;
    calculating, with a processor within the medical system, a first composite value using first sensor measurements from at least two sensors of the plurality of sensors;
    comparing the first composite value to a first threshold or a first specified range;
    if the first composite value exceeds the first threshold or is outside of the first specified range, then calculating, with the processor, a second composite value using second sensor measurements from at least a third sensor of the plurality of sensors, wherein the third sensor is different than the at least two sensors of the plurality of sensors used to calculate the first composite value;
    comparing the second composite value to a second threshold or a second specified range; and
    if the second composite value exceeds the second threshold or is outside of the second specified range, generating a worsening heart failure indicator via the processor within the medical system, the worsening heart failure indicating a likelihood that the patient's heart failure status has worsened,
    wherein calculating the first composite value includes either subtracting a first long-term average of the sensor measurements from the at least two sensors from a first short-term average of the sensor measurements from the at least two sensors, or subtracting a first baseline value of the sensor measurements from the at least two sensors from the first long-term average of the sensor measurements from the at least two sensors, wherein the first short-term average is an average over a first plurality of days and the first long-term average is an average over a second plurality of days different from the first plurality of days, and wherein calculating the second composite value includes either subtracting a second long-term average of the sensor measurements from the at least the third sensor from a second short-term average of the sensor measurements from the at least the third sensor, or subtracting a second baseline value of the sensor measurements from the at least the third sensor from the second long-term average of the sensor measurements from the at least the third sensor, wherein the second short-term average is an average over a third plurality of days and the second long-term average is an average over a fourth plurality of days different from the third plurality of days.

2. The method of claim 1 wherein the first and second specified ranges can be modified by a caregiver.

3. The method of claim 1 wherein the first and second specified ranges are modified by an algorithm based on one of the group consisting of patient population, age of the patient, gender of the patient and event information of the patient.

4. The method of claim 1 wherein the first composite value is more sensitive of heart failure than the second composite value.

5. The method of claim 1 wherein the first composite value is an earlier marker of heart failure than the second composite value.

6. The method of claim 1 wherein the first composite value is a more power-cost-effective measure than the second composite value.

7. The method of claim 1 wherein the sensor measurements from the at least two sensors include measurements of one or more of: respiration rate, dyspnea, rapid shallow breathing index, heart sounds, or cardiac pressure; and the sensor measurements from the at least the third sensor include measurements of trans-thoracic impedance.

8. The method of claim 1 wherein one or both of the first and second composite value is calculated using a regression model.

9. The method of claim 1, wherein sensor measurements from the at least two sensors include heart sounds measurements collected from an accelerometer sensor or a microphone sensor configured to sense heart sounds, and the sensor measurements from the at least the third sensor include trans-thoracic impedance measurements collected from an impedance sensor configured to sense trans-thoracic impedance.

10. The method of claim 1, further comprising providing or modifying a therapy based on the detected worsening heart failure indicator.

11. A system for detecting heart failure in a patient, comprising:
a plurality of sensors configured to collect sensor measurements of physiological data from a patient;
a processor configured to:
calculate a first composite value using sensor measurements from at least two sensors of the plurality of sensors; and
calculate a second composite value using sensor measurements from at least a third sensor of the plurality of sensors if the first composite value exceeds a first threshold or is outside of a first specified range, wherein the third sensor is different than the at least two sensors of the plurality of sensors used to calculate the first composite value; and a heart failure detection module configured to generate a worsening heart failure indicator that indicates a likelihood that the patient's heart failure status has worsened using at least the second composite value, wherein the processor is configured to calculate the first composite value by either subtracting a first long-term average of the sensor measurements from the at least two sensors from a first short-term average of the sensor measurements from the at least two sensors, or subtracting a first baseline value of the sensor measurements from the at least two sensors from the first long-term average of the sensor measurements from the at least two sensors, wherein the first short-term average is an average over a first plurality of days and the first long-term average is an average over a second plurality of days different from the first plurality of days, and wherein the processor is configured to calculate the second composite value by either subtracting a second long-term average of the sensor measurements from the at least the third sensor from a second short-term average of the sensor measurements from the at least the third sensor, or subtracting a second baseline value of the sensor measurements from the at least the third sensor from the second long-term average of the sensor measurements from the at least the third sensor, wherein the second short-term average is an average over a third plurality of days and the second long-term average is an average over a fourth plurality of days different from the third plurality of days.

12. The system of claim 11 wherein the second composite value is calculated based on current and past values for trans-thoracic impedance over a period of time.

13. The system of claim 11, wherein the at least two sensors include a cardiac electrical sensor and an accelerometer.

14. The system of claim 11, wherein the at least two sensors include an impedance sensor and an accelerometer.

15. The system of claim 11, wherein the at least the third sensor includes two or more sensors different from the two or more sensors used to calculate the first composite value.

16. A method of detecting heart failure in a patient via a medical system, comprising:
collecting sensor measurements of physiological data from a patient using a plurality of sensors, wherein at least one of the plurality of sensors resides on a cardiac rhythm management device;
calculating, with a processor within the medical system, a first composite value using sensor measurements from at least two sensors of the plurality of sensors, wherein the first composite value is an indication of a likelihood that the patient's heart failure status has changed;
comparing the first composite value to a first threshold or a first specified range;
if the first composite value exceeds the first threshold or is outside of the first specified range, then calculating a second composite value using sensor measurements from at least a third sensor of the plurality of sensors, wherein the third sensor is different than the at least two sensors of the plurality of sensors used to calculate the first composite value, wherein the second composite value is an indication of a likelihood that the patient's heart failure status has changed;
comparing the second composite value to a second threshold or a second specified range; and
if the second composite value exceeds the second threshold or is outside of the second specified range, generating a worsening heart failure indicator via the processor within the medical system, the worsening heart failure indicator indicating a likelihood that the patient's heart failure status has worsened;

wherein calculating the first composite value includes either subtracting a first long-term average of the sensor measurements from the at least two sensors from a first short-term average of the sensor measurements from the at least two sensors, or subtracting a first baseline value of the sensor measurements from the at least two sensors from the first long-term average of the sensor measurements from the at least two sensors, wherein the first short-term average is an average over a first plurality of days and the first long-term average is an average over a second plurality of days different from the first plurality of days, and wherein calculating the second composite value includes either subtracting a second long term average of the sensor measurements from the at least the third sensor from a second short-term average of the sensor measurements from the at least the third sensor, or subtracting a second baseline value of the sensor measurements from the at least the third sensor from the second long term average of the sensor measurements from the at least the third sensor, wherein the second short-term average is an average over a third plurality of days and the second long-term average is an average over a fourth plurality of days different from the third plurality of days.

* * * * *